(12) United States Patent
Matsubara et al.

(10) Patent No.: US 10,874,409 B2
(45) Date of Patent: Dec. 29, 2020

(54) METHODS AND SYSTEMS FOR CLEARING THROMBUS FROM A VASCULAR ACCESS SITE

(71) Applicant: VOLCANO CORPORATION, San Diego, CA (US)

(72) Inventors: Bradley S. Matsubara, Escondido, CA (US); John Unser, Temecula, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 962 days.

(21) Appl. No.: 14/596,880

(22) Filed: Jan. 14, 2015

(65) Prior Publication Data
US 2015/0196309 A1    Jul. 16, 2015

Related U.S. Application Data

(60) Provisional application No. 61/927,031, filed on Jan. 14, 2014.

(51) Int. Cl.
*A61B 17/22*    (2006.01)
*A61M 1/36*    (2006.01)
(Continued)

(52) U.S. Cl.
CPC ............ *A61B 17/22* (2013.01); *A61B 8/085* (2013.01); *A61B 8/0891* (2013.01); *A61B 8/12* (2013.01);
(Continued)

(58) Field of Classification Search
CPC ............... A61B 17/22; A61B 17/2202; A61B 17/32037; A61B 2017/22001; A61B 2090/3784; A61B 2217/005; A61B 2217/007; A61B 5/0066; A61B 5/0095; A61B 8/085; A61B 8/0891; A61B 8/12; A61B 8/445; A61B 8/4461; A61B 8/4488; A61M 1/3655; A61M 25/104; A61M 3/02
See application file for complete search history.

(56) References Cited

U.S. PATENT DOCUMENTS 4,794,931 A    1/1989 Yock
4,841,977 A    6/1989 Griffith et al.
(Continued)

FOREIGN PATENT DOCUMENTS

CA    2 616 760 A1    2/2007
EP    1 820 436 A2    8/2007
(Continued)

OTHER PUBLICATIONS

International Search Report and Written Opinion dated Apr. 10, 2015, for International Patent Application No. PCT/US2015/011397, filed Jan. 14, 2015 (14 pages).
(Continued)

*Primary Examiner* — Mark D Remaly

(57) ABSTRACT

The invention provides methods and systems for increasing the open cross-section of a vascular fistula that is obstructed by thrombus. Using a catheter having an imaging element and a thrombus disrupting element, the thrombus can be disrupted and removed, and the fistula evaluated with the imaging element. The imaging element is preferably an ultrasound imaging element.

10 Claims, 7 Drawing Sheets

(51) Int. Cl.
  *A61B 8/12* (2006.01)
  *A61B 8/08* (2006.01)
  *A61M 25/10* (2013.01)
  *A61B 8/00* (2006.01)
  *A61B 5/00* (2006.01)
  *A61B 17/3203* (2006.01)
  *A61B 90/00* (2016.01)

(52) U.S. Cl.
  CPC .......... *A61B 8/445* (2013.01); *A61B 17/2202* (2013.01); *A61M 1/3655* (2013.01); *A61M 25/104* (2013.01); *A61B 5/0066* (2013.01); *A61B 5/0095* (2013.01); *A61B 8/4461* (2013.01); *A61B 8/4488* (2013.01); *A61B 17/32037* (2013.01); *A61B 2017/22001* (2013.01); *A61B 2090/3784* (2016.02); *A61B 2217/005* (2013.01); *A61B 2217/007* (2013.01)

(56) References Cited

U.S. PATENT DOCUMENTS

| | | |
|---|---|---|
| 4,917,097 A | 4/1990 | Proudian et al. |
| 4,951,677 A | 8/1990 | Crowley et al. |
| 5,000,185 A | 3/1991 | Yock |
| 5,095,911 A | 3/1992 | Pomeranz |
| 5,125,137 A | 6/1992 | Corl et al. |
| 5,135,486 A | 8/1992 | Eberle et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Born et al. |
| 5,178,159 A | 1/1993 | Christian |
| 5,183,048 A | 2/1993 | Eberle |
| 5,226,421 A | 7/1993 | Frisbie et al. |
| 5,240,003 A | 8/1993 | Lancee et al. |
| 5,240,437 A | 8/1993 | Christian |
| 5,243,988 A | 9/1993 | Sieben et al. |
| 5,313,949 A | 5/1994 | Yock |
| 5,321,501 A | 6/1994 | Swanson et al. |
| 5,326,342 A | 7/1994 | Pflueger et al. |
| 5,348,017 A | 9/1994 | Thornton et al. |
| 5,353,798 A | 10/1994 | Sieben |
| 5,368,037 A | 11/1994 | Eberle et al. |
| 5,372,138 A | 12/1994 | Crowley et al. |
| 5,373,845 A | 12/1994 | Gardineer et al. |
| 5,373,849 A | 12/1994 | Maroney et al. |
| 5,375,602 A | 12/1994 | Lancee et al. |
| 5,453,575 A | 9/1995 | O'Donnell et al. |
| 5,771,895 A | 6/1998 | Slager |
| 5,830,222 A | 11/1998 | Makower |
| 5,873,835 A | 2/1999 | Hastings et al. |
| 6,068,638 A | 5/2000 | Makower |
| 6,106,476 A | 8/2000 | Corl et al. |
| 6,134,003 A | 10/2000 | Tearney et al. |
| 6,159,225 A | 12/2000 | Makower |
| 6,190,353 B1 | 2/2001 | Makower et al. |
| 6,200,268 B1 | 3/2001 | Vince et al. |
| 6,210,339 B1 | 4/2001 | Kiepen et al. |
| 6,283,951 B1 | 9/2001 | Flaherty et al. |
| 6,375,615 B1 | 4/2002 | Flaherty et al. |
| 6,381,350 B1 | 4/2002 | Klingensmith et al. |
| 6,421,164 B2 | 7/2002 | Tearney et al. |
| 6,457,365 B1 | 10/2002 | Stephens et al. |
| 6,508,824 B1 | 1/2003 | Flaherty et al. |
| 6,544,230 B1 | 4/2003 | Flaherty et al. |
| 6,551,250 B2 | 4/2003 | Khalil |
| 6,579,311 B1 | 6/2003 | Makower |
| 6,602,241 B2 | 8/2003 | Makower et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,709,444 B1 | 3/2004 | Makower |
| 6,726,677 B1 | 4/2004 | Flaherty et al. |
| 6,746,464 B1 | 6/2004 | Makower |
| 6,780,157 B2 | 8/2004 | Stephens et al. |
| 7,074,188 B2 | 7/2006 | Nair et al. |
| 7,175,597 B2 | 2/2007 | Vince et al. |
| 7,215,802 B2 | 5/2007 | Klingensmith et al. |
| 7,245,789 B2 | 7/2007 | Bates et al. |
| 7,359,554 B2 | 4/2008 | Klingensmith et al. |
| 7,387,636 B2 | 6/2008 | Cohn et al. |
| 7,447,388 B2 | 11/2008 | Bates et al. |
| 7,463,759 B2 | 12/2008 | Klingensmith et al. |
| 7,527,594 B2 | 5/2009 | Vardi et al. |
| 7,660,492 B2 | 2/2010 | Bates et al. |
| 7,736,317 B2 | 6/2010 | Stephens et al. |
| 7,783,337 B2 | 8/2010 | Feldman et al. |
| 7,787,127 B2 | 8/2010 | Galle et al. |
| 7,995,210 B2 | 8/2011 | Tearney et al. |
| 7,999,938 B2 | 8/2011 | Wang |
| 8,059,923 B2 | 11/2011 | Bates et al. |
| 8,108,030 B2 | 1/2012 | Castella et al. |
| 8,486,062 B2 | 7/2013 | Belhe et al. |
| 8,486,063 B2 | 7/2013 | Werneth et al. |
| 2002/0010487 A1 | 1/2002 | Evans et al. |
| 2004/0146546 A1 | 7/2004 | Gravett et al. |
| 2005/0196026 A1 | 9/2005 | Klingensmith et al. |
| 2005/0249391 A1 | 11/2005 | Kimmel et al. |
| 2006/0241342 A1 | 10/2006 | Macaulay et al. |
| 2007/0016034 A1 | 1/2007 | Donaldson |
| 2007/0232933 A1 | 10/2007 | Gille et al. |
| 2008/0119739 A1 | 5/2008 | Vardi et al. |
| 2008/0171944 A1 | 7/2008 | Brenneman et al. |
| 2008/0180683 A1 | 7/2008 | Kemp |
| 2008/0291463 A1 | 11/2008 | Milner et al. |
| 2009/0018393 A1 | 1/2009 | Dick et al. |
| 2009/0024085 A1 | 1/2009 | To et al. |
| 2009/0043191 A1 | 2/2009 | Castella et al. |
| 2009/0088650 A1 | 4/2009 | Corl |
| 2009/0195514 A1 | 8/2009 | Glynn et al. |
| 2009/0284332 A1 | 11/2009 | Moore et al. |
| 2010/0087732 A1 | 4/2010 | Eberle et al. |
| 2010/0130836 A1* | 5/2010 | Malchano ............... A61B 1/05 600/301 |
| 2010/0130864 A1 | 5/2010 | Donnelly et al. |
| 2010/0220334 A1 | 9/2010 | Condit et al. |
| 2011/0060229 A1 | 3/2011 | Hulvershorn et al. |
| 2011/0152683 A1* | 6/2011 | Gerrans ............ A61B 17/22012 600/435 |
| 2011/0152771 A1 | 6/2011 | Milner et al. |
| 2011/0306995 A1 | 12/2011 | Moberg |
| 2011/0319752 A1 | 12/2011 | Steinberg et al. |
| 2012/0108943 A1 | 5/2012 | Bates et al. |
| 2012/0230565 A1 | 9/2012 | Steinberg et al. |
| 2012/0283569 A1* | 11/2012 | Ciompi ............... A61B 8/0891 600/463 |
| 2013/0030295 A1 | 1/2013 | Huennekens et al. |
| 2013/0030303 A1 | 1/2013 | Ahmed et al. |
| 2013/0046167 A1 | 2/2013 | Shah |
| 2013/0137980 A1 | 5/2013 | Waters et al. |
| 2013/0296704 A1 | 11/2013 | Magnin et al. |
| 2013/0303907 A1 | 11/2013 | Corl |
| 2014/0018678 A1* | 1/2014 | Donnelly ............ A61B 5/02007 600/438 |
| 2014/0180126 A1* | 6/2014 | Millett ................. A61B 8/4494 600/467 |

FOREIGN PATENT DOCUMENTS

| | | |
|---|---|---|
| WO | 91/17710 A1 | 11/1991 |
| WO | 03/030744 A1 | 4/2003 |
| WO | 2014/100226 A1 | 6/2014 |
| WO | 2014/109879 A1 | 7/2014 |
| WO | 2014/143816 A1 | 9/2014 |
| WO | 2014/150401 A1 | 9/2014 |

OTHER PUBLICATIONS

Anonymous, 2006, Clinical Practice Guidelines and Clinical Practice Recommendations 2006 Updates, National Kidney Foundation:10PP.

(56) References Cited

OTHER PUBLICATIONS

International Search Report and Written Opinion dated May 4, 2015, for International Patent Application No. PCT/US2015/011337, filed Jan. 14, 2015 (16 pages).
International Search Report and Written Opinion dated Apr. 28, 2015, for International Patent Application No. PCT/US2015/011357, filed Jan. 14, 2015 (11 pages).
International Search Report and Written Opinion dated Apr. 21, 2015, for International Patent Application No. PCT/US2015/011359, filed Jan. 14, 2015 (10 pages).
International Search Report and Written Opinion dated Apr. 28, 2015, for International Patent Application No. PCT/US2015/011411, filed Jan. 14, 2015 (11 pages).
Toregeani et al., Evaluation of hemodialysis arteriovenous fistula maturation by color-flow Doppler ultrasound, J Vasc Bras 7(3):203-2013, 2008.
Ferring, et al., Vascular ultrasound for the pre-operative evaluation prior to arteriovenous fistula formation for haemodialysis: review of the evidence, Nephrol. Dial. Transplant. 23(6):1809-1815, 2008.
Robbin, et al., Hemodialysis arteriovenous fistula maturity: US evaluation, Radiology 225(1):59-64, 2002.
Harrison et al., What's in a name?, J Endo Ther 14(6):797-801, 2011.
West et al., Arterial insufficiency in hemodialysis access procedures: correction by banding technique, Transpl Proc 23 (2): 1838-40, 1991.
Rivers, et al., 1992, Correction of steal syndrome secondary to hemodialysis access fistulas: a simplified quantitative technique, Surgery 112(3):593-7.
Kirkman, 1991, Technique for flow reduction in dialysis access fistulas, Surg Gyn Obstet 172(3):231-3.
Mickley, 2008, Steal Syndrome-strategies to preserve vascular access and extremity, Nephrol Dial Transplant 23:19-24.
Miller et al. 2006, Minimally Invasive Limited Ligation Endoluminal-assisted Revision (MILLER) for treatment of dialysis access-associated steal syndrome, Kidney Int 70(4):765-70.
Schneider, et al., 2006, T-banding: A technique for flow reduction of a hyper-functioning arteriovenous fistula, J Vasc Surg.
Miller, et al., 2009, The MILLER banding procedure is an effective method for treating dialysis-associated steal syndrome, Kidney Int 1-8.
Wang et al., "Optimizing the Beam Pattern of a Forward-Viewing Ring-Annular Ultrasound Array for Intravascular Imaging", Transactions on Ultrasonics, Ferroelectrics, and Frequency Control, vol. 49, No. 12, Dec. 2002.
Fleming et al., "Real-time monitoring of cardiac radio-frequency ablation lesion formation using an optical coherence tomography forward-imaging catheter.," J. Biomed. Opt. 15, (3 ), 030516-030513 (2010).
Wang et al. "In vivo intracardiac optical coherence tomography imaging through percutaneous access: toward image-guided radio-frequency ablation". J. Biomed. Opt. 0001;16(11):110505-110505-3. doi:10.1117/1.3656966.
Seward et al., Mayo Clinic Proceedings 71(7):629-635 (1996).
Bail et al.; 'Optical coherence tomography with the "Spectral Radar"—Fast optical analysis in volume scatterers by short coherence interferometry' Optics letters vol. 21, No. 14 (1996) 1087-1089.
Smith et al., 'Absolute displacement measurements using modulation of the spectrum of white light in a Michelson interferometer' Applied Optics, vol. 28, No. 15, 1989, 3339-3342.

\* cited by examiner

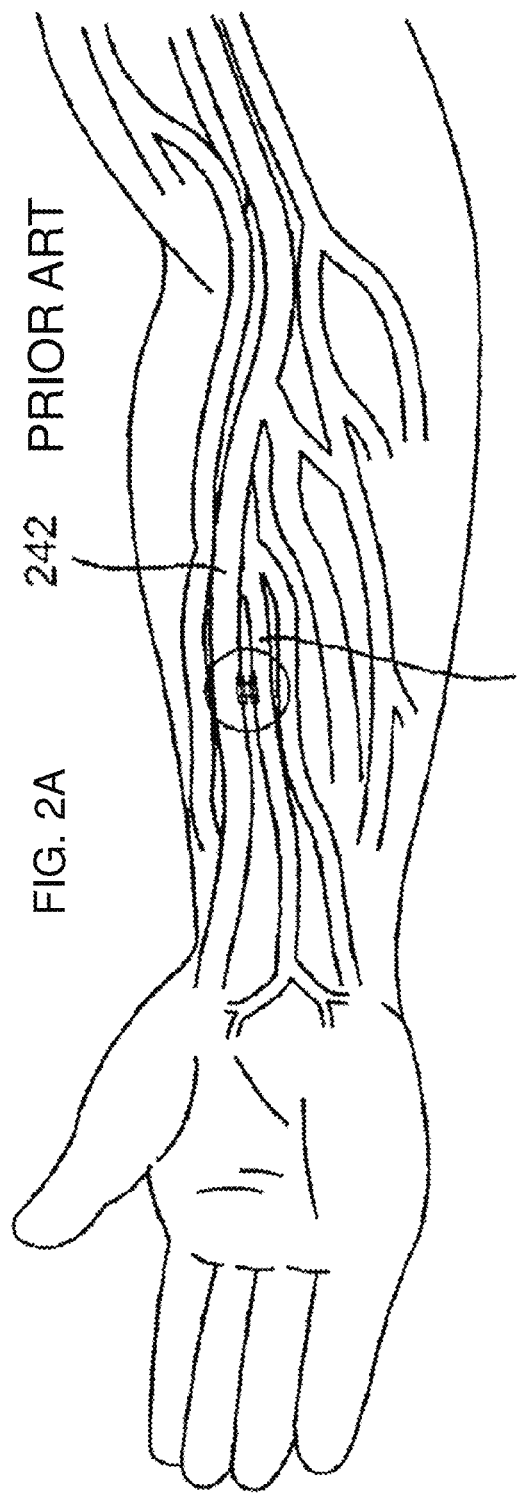
FIG. 2A  242  PRIOR ART
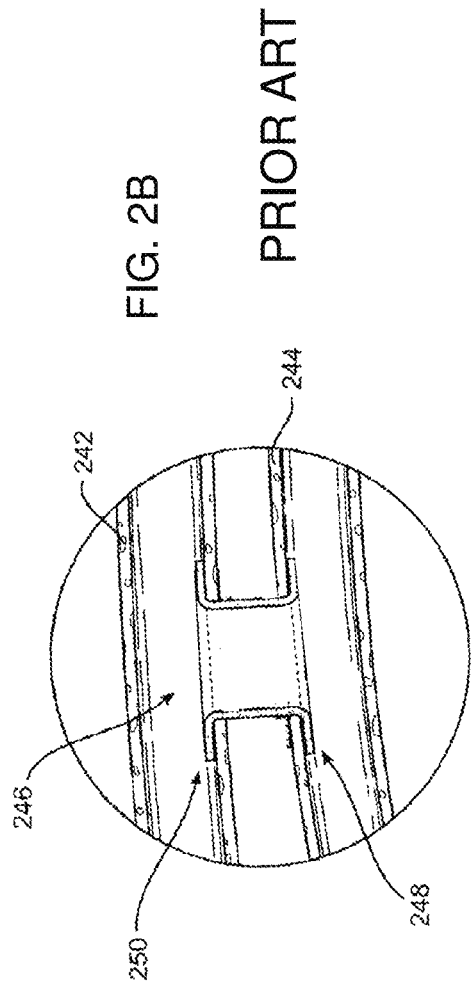
FIG. 2B  PRIOR ART

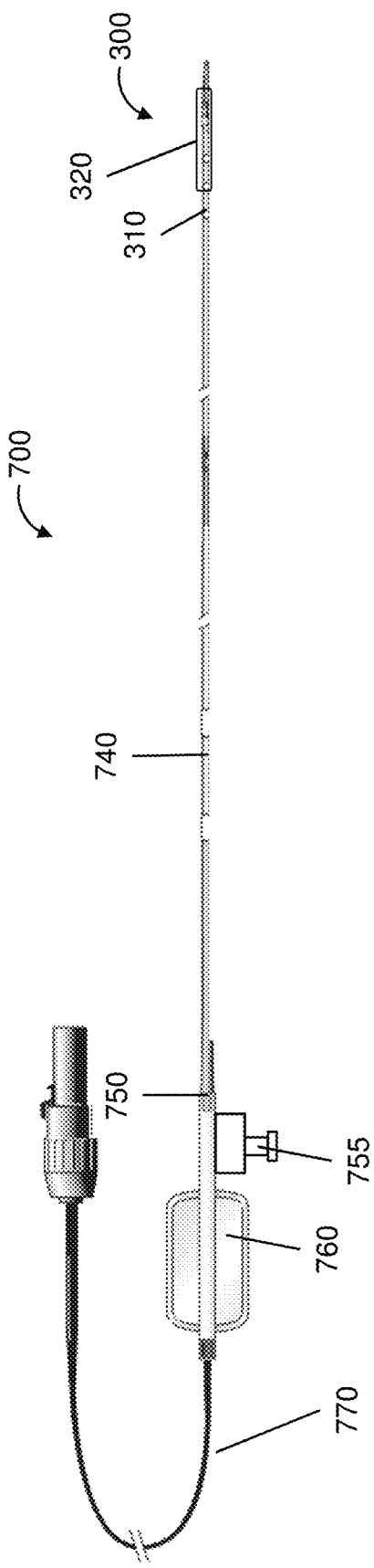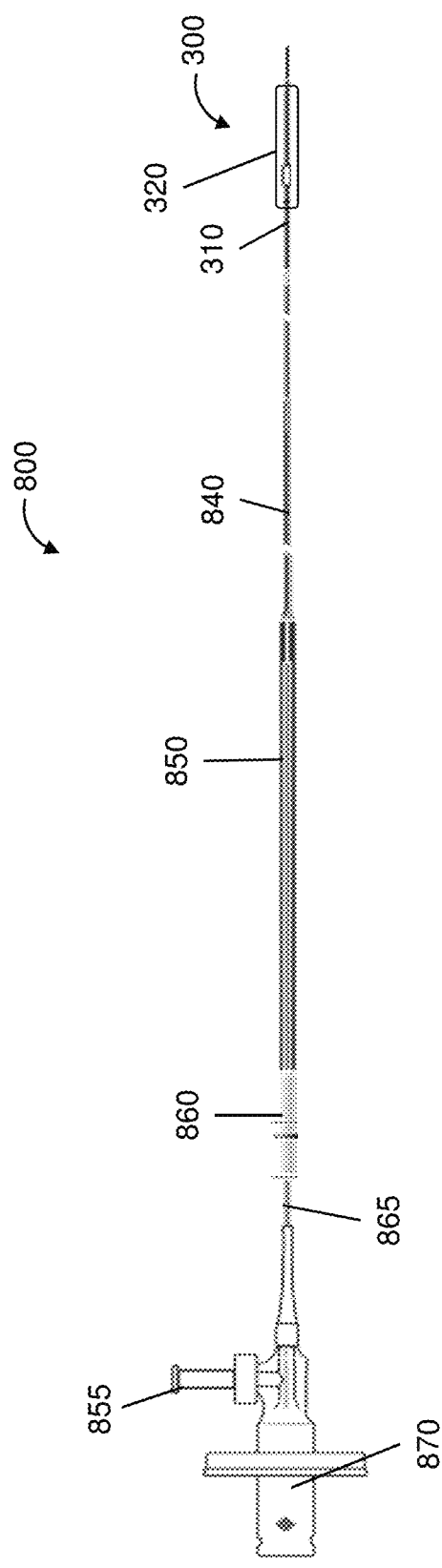

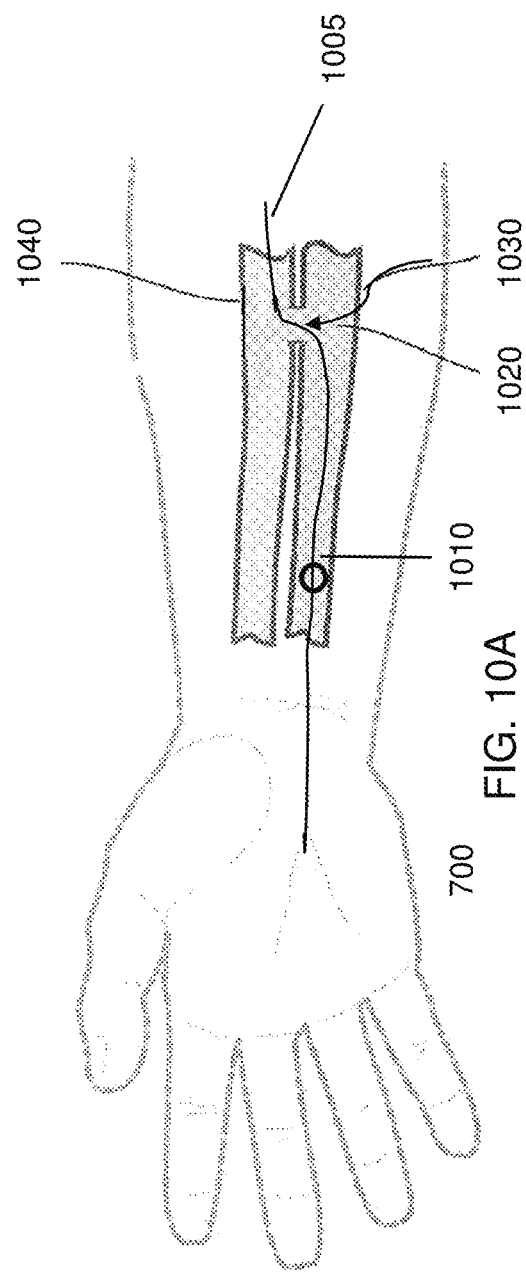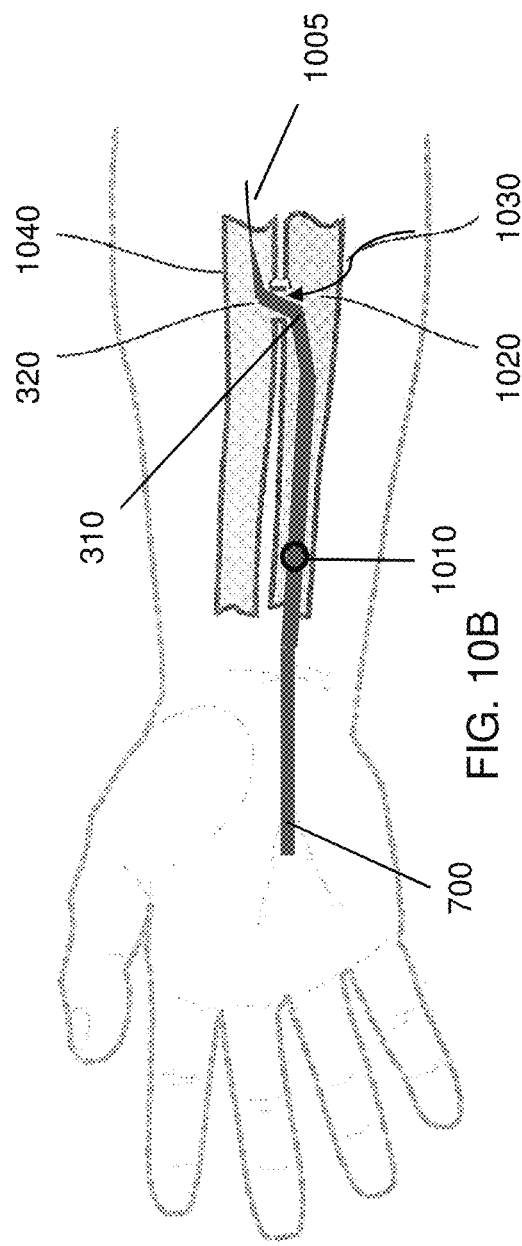

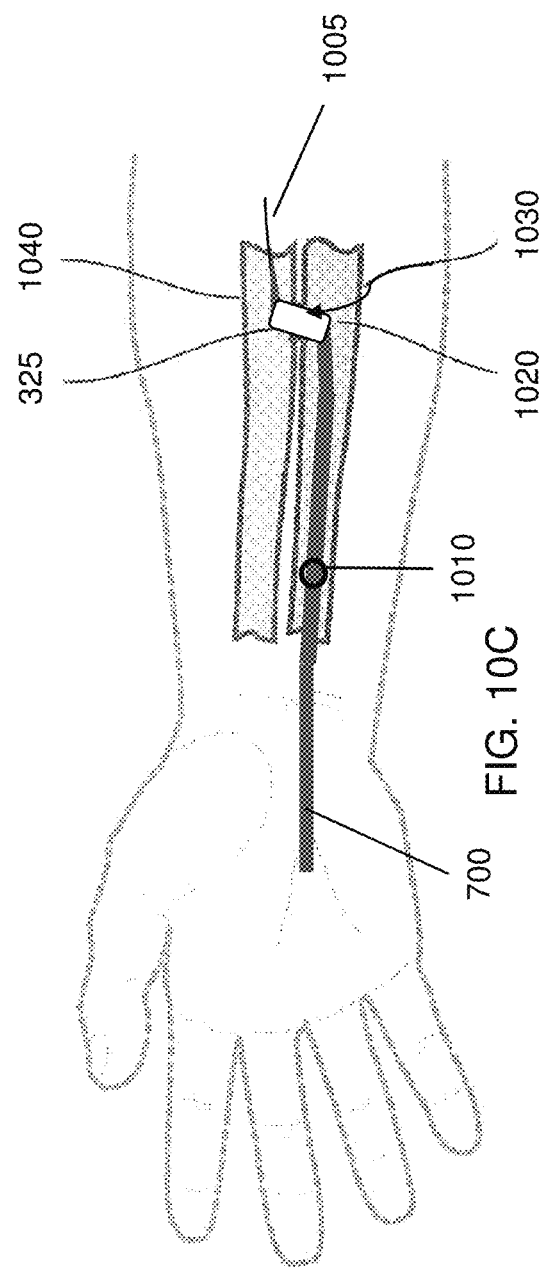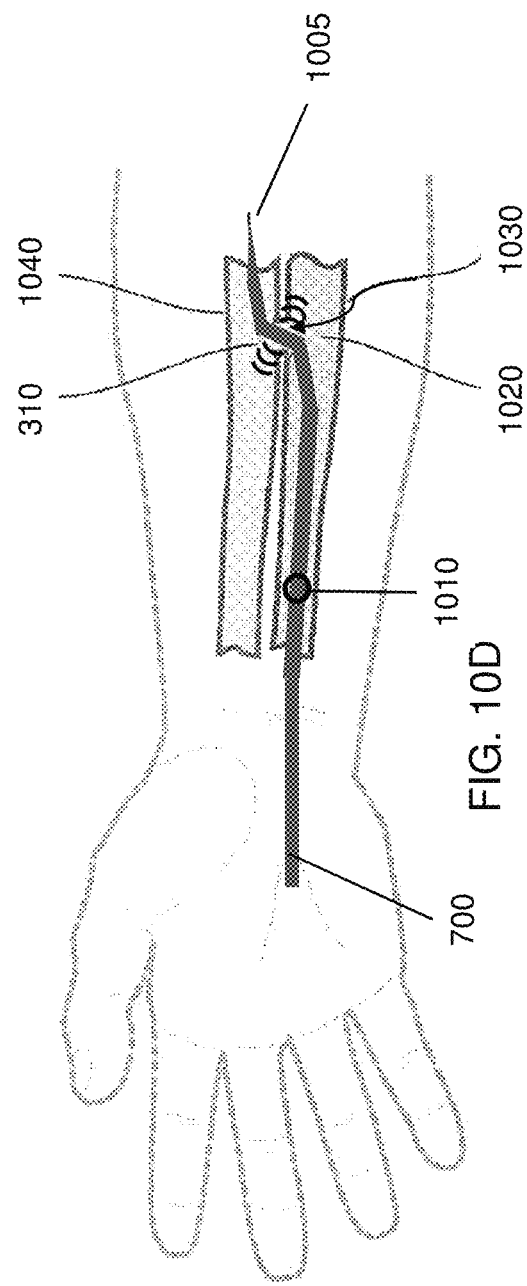

METHODS AND SYSTEMS FOR CLEARING THROMBUS FROM A VASCULAR ACCESS SITE

CROSS-REFERENCE TO RELATED APPLICATIONS

This application claims the benefit of, and priority to, U.S. Provisional Application Ser. No. 61/927,031, filed Jan. 14, 2014, the content of which is incorporated by reference herein in its entirety.

FIELD OF THE INVENTION

The invention relates to vascular fistulas, and methods for removing thrombus from vascular fistulas.

BACKGROUND

Hemodialysis is commonly used to clean the blood of a patient having compromised kidney function as a result of disease or injury. Hemodialysis is accomplished with a dialysis machine that essentially serves as an artificial kidney by removing the by-products of metabolism, as well as excess water, from the blood. The machine typically includes a filter, constructed from semipermeable membranes, and a pump. The semipermeable membranes are arranged in multiple pleated sheets or small caliber tubes to increase the surface area across which dialysis takes place, as shown in FIG. 1. The pump pulls blood from the patient through one line (afferent line 110) and returns the blood through a second line (efferent line 120). The same pump also pressurizes the blood to overcome the resistance caused by the membrane.

For multiple reasons, the dialysis process is time sensitive. First, blood must be returned to the patient as rapidly as it is withdrawn to avoid complications from large fluctuations in intravascular volume, i.e., organ damage or shock. Secondly, dialysis patients typically need to undergo treatment at least three times per week, thus a lengthy dialysis procedure will limit a patient's productive hours. Accordingly, the afferent 110 and efferent 120 connections are typically coupled to large-bore, high-flow blood vessels (located in a limb) by way of transcutaneous catheters, such as shown in FIG. 1. To perform hemodialysis, two large bore needles are sterilely introduced into the blood vessels through the intact skin. The large lumen and high blood flow provide excellent drainage for dialysis. After hemodialysis is completed, the needles are removed, so no permanent breech in the skin exists. Each time the patient is dialyzed, needles are reintroduced.

In order to speed the dialysis process, the peripheral vessels of the limb are typically bypassed by creating a fistula 1030 between larger vessels in the limb, e.g., as shown in FIGS. 1 and 2A/B. This surgically created "short circuit" in the circulatory system may be referred to as a shunt. The low resistance in the shunt allows higher blood flows through the dialysis machine.

In some instances, the fistula is merely a connection between a closely-spaced artery and vein, e.g., between the brachial artery 1030 and the antecubital veinas 1020, as shown in FIG. 1. Fistula creation can be accomplished by creating an incision in the limb, dissecting the vessels, creating a small opening (anastomosis) in both vessels and then suturing the openings together. Alternatively, devices such as disclosed in U.S. Patent Publication No. 2008/0171944 and U.S. Pat. No. 7,387,636 can be used to create a vascular fistula using intravascular access. (U.S. Patent Publication No. 2008/0171944 and U.S. Pat. No. 7,387,636 are incorporated by reference herein in their entireties.)

In some instances, it is not possible to connect two closely-spaced vessels, thus an artificial or autologous graft is used to join the vessels, as shown in FIGS. 2A and 2B. Like the technique described above, an incision is made, the vessels are dissected, and anastomoses are formed. Unlike the previous method, a secondary lumen, i.e., a graft 246, is used to join the openings in the two vessels, as shown in detail in FIG. 2A/B. This method has the advantage of allowing larger vessels to be coupled when the larger vessels cannot be brought into direct connection. An additional benefit is that that graft is easily palpated, and provides a way to quickly assess the health of the shunt. The graft may be synthetic, the graft may be from another source, e.g., a cadaver, or the graft may be from the patient undergoing dialysis (an autologous graft). As a result of this graft 246, blood flowing through the vessels bypasses the capillary bed(s), and as such, represents a very low resistance pathway. Accordingly, a larger volume of blood can be cleaned during a typical 4-hour dialysis cycle.

One problem with fistulas, as described above, is the growth of thrombus or other deposits in the vicinity of the fistula (with or without a graft), necessitating thrombectomy or revision/replacement of the fistula. In some instances, the wound from the fistula stimulates platelet activation and clot formation. In other instances, a patient may have a genetic predisposition to thickened vessels and/or plaque formation. In such instances, these growths narrow the open cross-section of the fistula resulting in decreased flow. Unfortunately, because patients with compromised kidneys cannot metabolize anticoagulants and thrombolytic agents, hemodialysis patients having narrowed fistulas require direct intervention via intravascular or open surgical procedures.

SUMMARY

The invention provides improved methods for removing thrombus from vascular fistulas, e.g., arteriovenous fistulas, e.g., Cimino-Brescia fistulas. Such techniques can be used to improve the patency of vascular fistulas, thus improving the efficiency of dialysis procedures. The techniques generally involve delivering a catheter comprising an imaging element and a thrombus disrupting element to the fistula and actuating the thrombus disrupting element to disrupt the thrombus and increase the open cross-section of the fistula. Because the catheter further includes an imaging element, it is possible to image the fistula before, after, or during the disrupting step. Once the fistula is imaged, it is possible to quantify the open cross-section of the fistula and assess the success of the procedure. In some embodiments, the method additionally includes displaying a cross-sectional image of the fistula. Because it is possible to immediately assess the fistula after the thrombectomy, a physician will know the status of the fistula prior to the next dialysis treatment, thereby avoiding dialysis complications due to incomplete thrombectomy. The methods are generally applicable to vascular fistulas, including fistulas comprising autologous graft tissues.

A variety of thrombus disrupting elements can be used with the methods of the invention. For example, the thrombus disrupting element can be an expandable element, e.g., an angioplasty balloon, whereby expanding the expandable element disrupts the fistula. Alternatively, the thrombus disrupting element could be an aspiration port coupled to an aspiration lumen, or having an angio-jet-type configuration whereby a high velocity fluid is used to dislodge thrombus and to produce negative pressure to aspirate the thrombus. In either instance, because the aspiration catheter additionally includes imaging capabilities, it is possible to immediately evaluate the fistula after the procedure, as described above for the catheter having an expandable element. Alternatively, the thrombus disruption element may comprise a plurality of irrigation ports to disrupt thrombus at a fistula with a pressurized irrigation fluid.

Depending upon the construction of the catheter, a surgeon using the method of the invention may employ one or more of a variety of imaging modalities to evaluate the fistula. For example, the imaging may be done with ultrasound, such as with a phased-array ultrasound transducer or with a rotational pullback ultrasound transducer. In other instances, the imaging may be done with visible light using evaluative techniques such as optical coherence tomography. In yet other instances, the fistula may be evaluated with digital imaging or with spectroscopic techniques. All of these imaging modalities provide additional information that helps a physician to determine the success of the procedure and the long-term prognosis for the fistula.

The invention additionally includes a system for delivering treatment to a vascular fistula having thrombus, such as an arteriovenous fistula. The system includes a catheter having an imaging element and a thrombus disruption element, an imaging controller operatively coupled to the imaging element, and a disruption element controller coupled to the thrombus disruption element. The imaging element is configured to cause the imaging element to image a vascular fistula, either before, after, or during actuation of the thrombus disruption element. The disruption element controller is configured to cause the thrombus disruption element to actuate, e.g., by inflating a balloon, producing a negative pressure at a distal port, or causing an irrigation fluid to be delivered to the thrombus. With this action, the thrombus is disrupted, increasing blood flow through the vascular fistula. Embodiments of the system may also comprise an image processor and a display to produce cross-sectional images of the fistula for viewing.

BRIEF DESCRIPTION OF THE DRAWINGS

It is understood that the drawings presented herein are exemplary of the invention, but do not limit the invention to particular configurations or a particular sequence of steps.

FIG. 2A shows an arteriovenous fistula in the forearm of a subject;

FIG. 2B shows an exploded view of the fistula of FIG. 2A, including a graft between an artery and a vein;

FIG. 7 shows an angioplasty balloon catheter comprising a phased-array ultrasound transducer, suitable for use with methods of the invention;

FIG. 8 shows an angioplasty balloon catheter comprising an ultrasound transducer that is configured to translate and rotate during imaging, suitable for use with methods of the invention;

FIG. 10A depicts the placement of a guide wire through a vascular fistula;

FIG. 10B depicts delivery of a catheter having a balloon and ultrasound imaging to a vascular fistula;

FIG. 10C depicts expansion of the balloon of the catheter of FIG. 10B, thus disrupting thrombus in the fistula;

FIG. 10D depicts ultrasound imaging of the fistula after disruption of thrombus, as shown in FIG. 10C.

DETAILED DESCRIPTION

Figure 1:
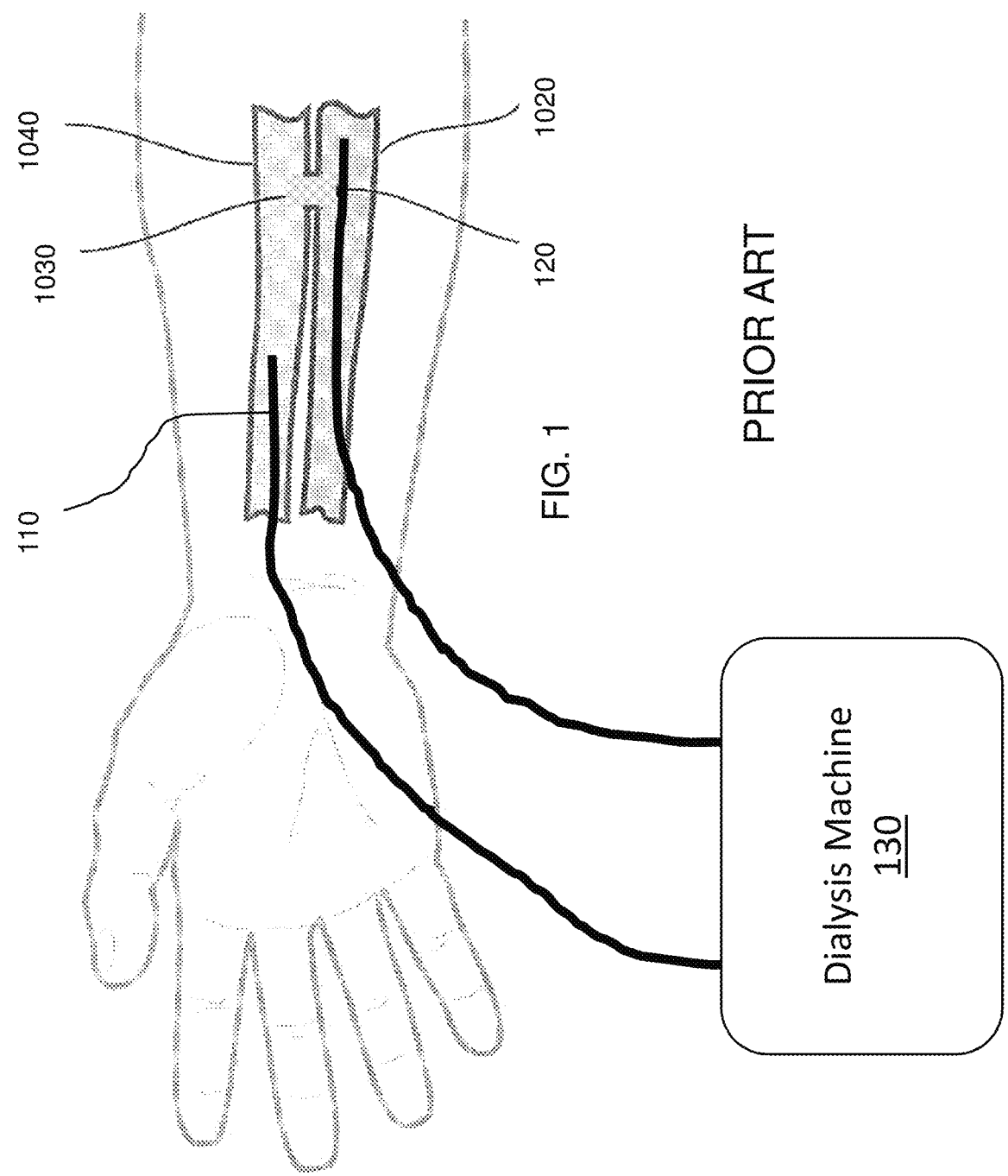
FIG. 1 depicts an arteriovenous fistula from the brachial artery to the antecubital veinas used to speed hemodialysis in a patient with compromised renal function.

The invention provides methods and systems for increasing the open cross-section of a vascular fistula that is obstructed by thrombus. Using a catheter having an imaging element and a thrombus disrupting element, the thrombus can be disrupted and removed, and the fistula evaluated with the imaging element. The imaging element is often an ultrasound imaging element.

As described in the Background, a vascular fistula, such as an arteriovenous fistula can be used to increase the effectiveness of hemodialysis. The methods and systems of the invention, described below, need not be limited to hemodialysis application, however, because the methods and systems are generally applicable for clearing and evaluating vascular grafts, e.g., as used in coronary bypass. It is also understood that the methods and systems are not limited to the removal of thrombus, because the methods and systems can be used for the removal of fatty accumulations and plaque from a vascular fistula.

A catheter suitable for use with the methods of the invention will include an imaging element and a thrombus disruption element. Catheters suitable for use with the invention typically include a guide wire lumen that allows the catheter to be directed to a point of treatment. The guide wire lumen may be a distinct guide wire lumen that runs the length of the catheter. In other embodiments, the guide wire lumen may only run a portion of the length of the catheter, e.g., a "rapid exchange" guide wire lumen. The guide wire lumen may be situated on top of the therapeutic delivery lumen or the guide wire channel could be side-by-side the therapeutic delivery lumen. In other cases, it may be possible to provide a fixed or integral coil tip or guide wire tip on the distal portion of the catheter or even dispense with the guide wire entirely. For convenience of illustration, guide wires will not be shown in all embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of fistula treatment catheters, the length is typically in the range from 60 cm to 150 cm, the diameter is preferably below 8 French, more preferably below 7 French, and most preferably in the range from 2 French to 7 French.

Catheter bodies will typically be composed of a biocompatible polymer that is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques.

The distal portion of the catheters of the present invention may have a wide variety of forms and structures depending upon the desired method of imaging and thrombus disruption. A plurality of different distal portions 300, 400, 500, 600 of catheters are shown in FIGS. 3-6. Each distal portion 300, 400, 500, 600 includes an imaging element 310, 410, 510, 610 and a thrombus disruption element 320, 420, 520, 620. The imaging element 310, 410, 510, 610 in FIGS. 2-6 is depicted as a phased array intravascular ultrasound (IVUS) transducer, however, other imaging modalities, such as OCT or visible imaging could also be used, as discussed below. A phased-array imaging element includes a set of transducers that image the tissue with ultrasound energy (e.g., 20-50 MHz range) and a set of image collectors that collect the returned energy (echo) to create an intravascular image. The array is arranged in a cylindrical pattern, allowing the imaging element 310, 410, 510, 610 to image 360° inside a vessel. In some embodiment, the transducers producing the energy and the collectors receiving the echoes are the same elements, e.g., piezoelectric elements. The thrombus disruption elements may be a Fogarty-type angioplasty balloon 320 or other expanding element, or an aspiration lumen 420, an angio-jet type mechanism (520 and 525), or a plurality of irrigation ports 620. The distal portion 300, 400, 500, 600 may also include one or more radiopaque markers to facilitate identifying the location of the catheter with X-ray imaging, i.e., angiography or computed tomography.

An expanding disrupting element 320 may include a balloon constructed from a variety of materials, including polyethylene, nylon, polyvinylchloride, or polyethylene terephthalate. Because a fistula is typically smaller than, e.g., a major artery, the expanding disrupting element 320 is typically on the order of 2-7 French, i.e., approximately 1-3 mm in diameter, when in an unexpanded state. Once expanded, the expanding disrupting element may be on the order of 3-8 mm depending upon the pressure on the expanding element and the compliance of the material. In some embodiments, the expanding element will be constructed from a high-compliance material that is able to withstand pressures on the order of 6 to 10 atm. The expanding element may additionally include surface features such as ridges, studs, fins or protrusions to facilitate disruption of thrombus.

Figure 5:
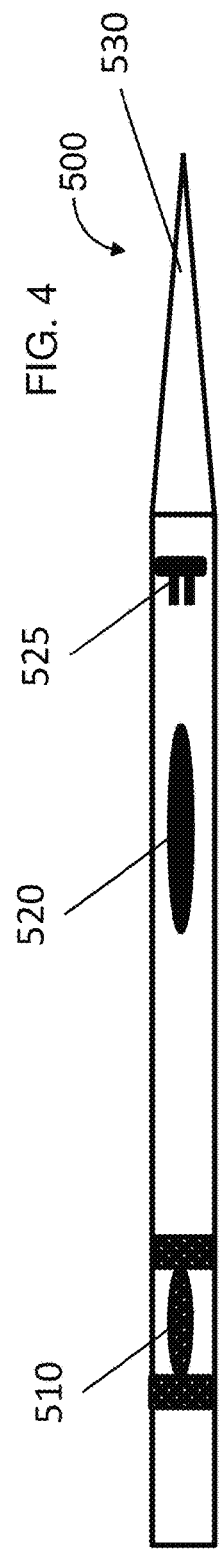
FIG. 5 depicts a distal end of a therapeutic catheter suitable for use with the invention. The catheter of FIG. 5 employs a high pressure jet to create negative pressure that disrupts and removes thrombus located in a fistula.

A variety of aspiration-type disrupting elements 420, 520 can be used with catheters of the invention. In one embodiment, the disrupting element can be a simple aspiration lumen 420 to which a negative pressure is provided, e.g., from a syringe or pump (not shown). While the aspiration lumen 420 is shown terminating at the distal tip in FIG. 4, the aspiration lumen 420 may also communicate with a side port, e.g., as shown in FIG. 5 to allow for the inclusion of a distal tip. Such a design may help reduce clogging when delivering the catheter to the fistula. Furthermore, advanced designs of a distal portion 500 may include jets 525 that provide a greater negative pressure in proximity to the aspiration port 520, and created high pressure flow in the vicinity of distal portion 500, thereby allowing for more effective disruption and removal of thrombus.

Figure 3:
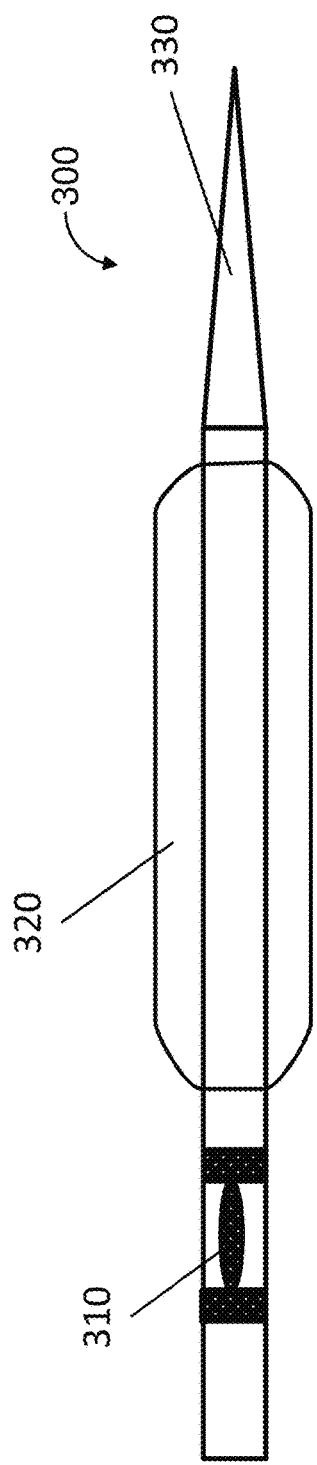
FIG. 3 depicts a distal end of a therapeutic catheter suitable for use with the invention. The catheter of FIG. 3 employs a balloon to disrupt thrombus located in a fistula.
Figure 4:
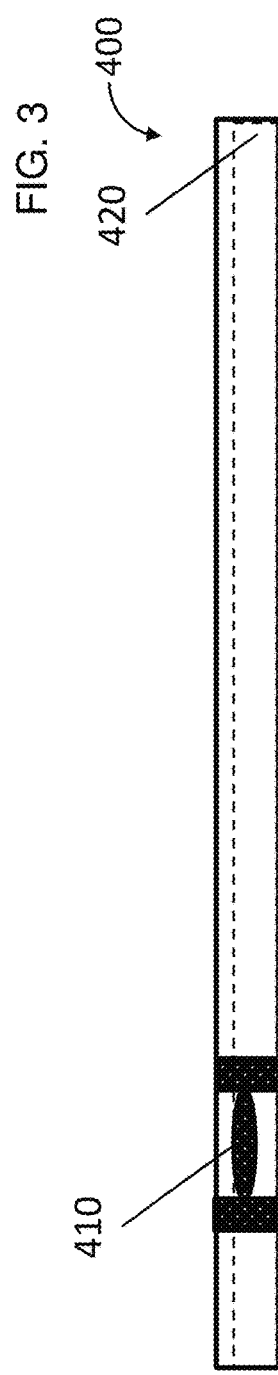
FIG. 4 depicts a distal end of a therapeutic catheter suitable for use with the invention. The catheter of FIG. 4 delivers negative pressure to an aspiration port at the distal end of the catheter to disrupt and remove thrombus located in a fistula.
Figure 6:
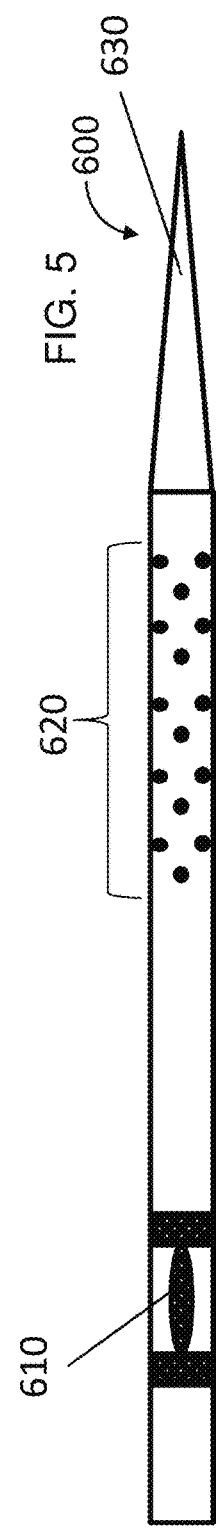
FIG. 6 depicts a distal end of a therapeutic catheter suitable for use with the invention. The catheter of FIG. 6 delivers an irrigation fluid from a plurality of irrigation ports to disrupt thrombus located in a fistula.

In another embodiment, the disrupting element includes a plurality of irrigation ports that are connected to an irrigation lumen traversing a catheter body and coupled to a source of irrigation fluid (not shown). The irrigation fluid is disbursed through the irrigation ports 620 at high pressure causing thrombus in a fistula to be broken up and cleared from the fistula. Catheters having an irrigating disrupting element may be used in conjunction with a separate aspiration catheter and/or a filter to assure As shown in FIGS. 3, 5, and 6, the catheter may include a flexible atraumatic distal tip 330, 530, 630 coupled to the rigid distal portion of the catheter. For example, an integrated distal tip 330, 530, 630 can increase the safety of the catheter by eliminating the joint between the distal tip and the catheter body. The integral tip can provide a smoother inner diameter for ease of tissue movement into a fistula. During manufacturing, the transition from the housing to the flexible distal tip can be finished with a polymer laminate over the material housing. No weld, crimp, or screw joint is usually required. The atraumatic distal tip 330, 530, 630 also permits advancing the catheter distally through the fistula while reducing any damage caused to the fistula by the catheter. Additionally, the distal tip 330, 530, 630 may have a guide wire lumen (not shown) to permit the catheter to be guided to the target tissue over a guide wire. In some exemplary configurations, the atraumatic distal tip 330, 530, 630 includes a coil. The distal tip 330, 530, 630 need not be cone shaped, however. In some configurations the distal tip 330, 530, 630 has a rounded, blunt end.

As mentioned previously, in some embodiments, the imaging assembly is an IVUS imaging assembly. The imaging assembly can be a phased array IVUS imaging assembly, an pull-back type IVUS imaging assembly, or an IVUS imaging assembly that uses photoacoustic materials to produce diagnostic ultrasound and/or receive reflected ultrasound for diagnostics. IVUS imaging assemblies and processing of IVUS data are described for example in Yock, U.S. Pat. Nos. 4,794,931, 5,000,185, and 5,313,949; Sieben et al., U.S. Pat. Nos. 5,243,988, and 5,353,798; Crowley et al., U.S. Pat. No. 4,951,677; Pomeranz, U.S. Pat. No. 5,095,911, Griffith et al., U.S. Pat. No. 4,841,977, Maroney et al., U.S. Pat. No. 5,373,849, Born et al., U.S. Pat. No. 5,176,141, Lancee et al., U.S. Pat. No. 5,240,003, Lancee et al., U.S. Pat. No. 5,375,602, Gardineer et at., U.S. Pat. No. 5,373,845, Seward et al., Mayo Clinic Proceedings 71(7): 629-635 (1996), Packer et al., Cardiostim Conference 833 (1994), "Ultrasound Cardioscopy," Eur. J.C.P.E. 4(2):193 (June 1994), Eberle et al., U.S. Pat. No. 5,453,575, Eberle et al., U.S. Pat. No. 5,368,037, Eberle et at., U.S. Pat. No. 5,183,048, Eberle et al., U.S. Pat. No. 5,167,233, Eberle et at., U.S. Pat. No. 4,917,097, Eberle et at., U.S. Pat. No. 5,135,486, and other references well known in the art relating to intraluminal ultrasound devices and modalities. All of these references are incorporated by reference herein.

In other embodiments, the imaging may use optical coherence tomography (OCT). OCT is a medical imaging methodology using a miniaturized near infrared light-emitting probe, and is capable of acquiring micrometer-resolution, three-dimensional images from within optical scattering media (e.g., biological tissue). OCT systems and methods are generally described in Castella et al., U.S. Pat. No. 8,108,030, Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety.

In advanced embodiments, the systems of the invention incorporate focused acoustic computed tomography (FACT), which is described in WO2014/109879, incorporated herein by reference in its entirety.

In some embodiments, e.g., as shown in FIGS. 7 and 8, the imaging assembly uses intravascular ultrasound (IVUS). IVUS-imaging catheters may be array-type catheters, i.e., as depicted in FIG. 7, or IVUS-imaging catheters may be pull-back type catheters as depicted in FIG. 8. In some embodiments, an IVUS array is configured to image beyond the distal end of the catheter, i.e., "forward-looking" IVUS, or "FLIVUS." A phased-array catheter 700 is depicted in FIG. 7, and includes a distal portion 300, a middle portion, 740, and a proximal portion 750. The phase array catheter 700 additionally includes a side arm 755 for delivering fluid to expanding member 320, as well as a manipulator 760 and connector 770. A pull-back catheter 800 is depicted in FIG. 8, and includes a body having distal 300, middle 850, and proximal 860 portions. In the pull-back catheter 800 of FIG. 8, the imaging assembly 310 is located within a transparent portion of the distal 300, and is configured to move back and forth within the catheter and rotate. The pull-back catheter 800 additionally includes a side arm 755 for delivering fluid to expanding member 320. The imaging assembly 310 connects to interface 870, which provides an electrical connection (power and signal) and rotational motion to shaft 865, which is connected to imaging assembly 310. Pull-back catheter 800 can be interfaced to an imaging controller (not shown) and a disruption element controller (not shown) in order to control imaging element 310 as well as the disruption of thrombus. Variations on pull-back catheter 100 may include a source of therapeutic energy.

While the imaging element 310, 410, 510, 610 is depicted as located proximal to the disruption element 320, 420, 520, 620, the imaging element 310, 410, 510, 610 may also be located distal to the disruption element 320, 420, 520, 620. In some embodiments, the imaging element 310, 410, 510, 610 may be co-located with the disruption element 320, 420, 520, 620. Co-located imaging and disruption elements are especially suitable for expanding member configurations, such as shown in FIG. 3, because the balloon material can be chosen such that it is essentially transparent to the ultrasound waves. Additionally, a catheter may be configured with a pull-back imaging element that is able to survey the entirety of the expanded member while it is expanded.

Figure 9:
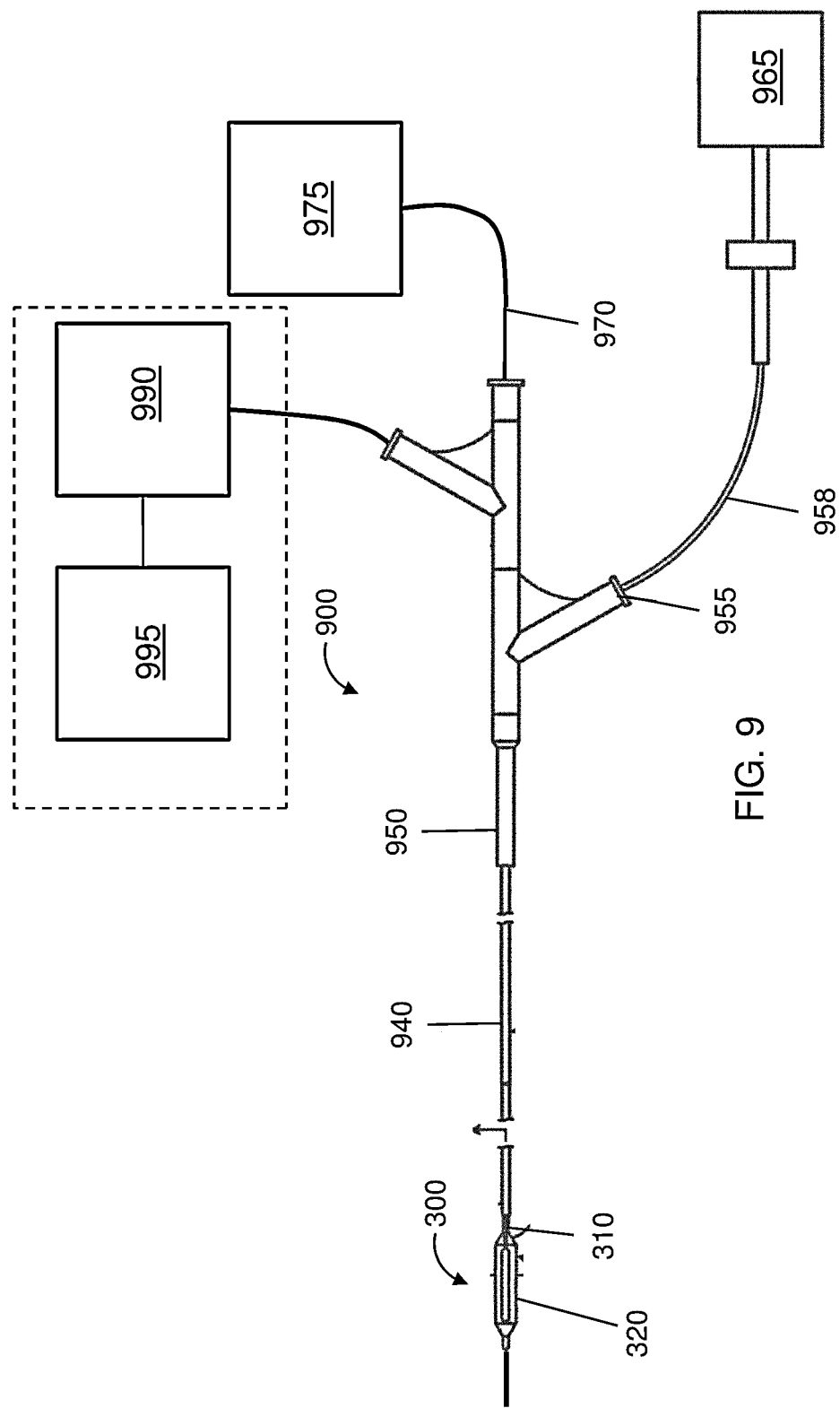
FIG. 9 depicts a system configured to increase the open cross-section in a vascular fistula.

A system of the invention including a catheter having imaging and disruption elements is shown in FIG. 9. The catheter 900 of FIG. 9 includes imaging element 310 and disruption element 320 at the distal end 300. The catheter 900 includes middle 940 and proximal 950 portions, and includes a side arm 955 that allows an expansion fluid to be delivered to the disruption element 320 via tube 958 coupled to disruption element controller 965 which includes a pump for pressurizing the expansion fluid and forcing it through tube 958. System 900 additionally includes an imaging element controller 975 that delivers power to the imaging element 310 and may coordinate a transducer supply signal, depending upon the configuration of the imaging element 310. In some embodiments, the system 900 additionally includes an image processing system 990 that receives image data from the imaging element 310 and processes the image data to create new data that represents an image that can be displayed on display 995. The image processing system 990 can be constructed from a general use computer having a processor, memory and instruction, however the image processor need not be a single stand-alone device, but may use distributed computing resources, such as cloud computing. While the system 900 is depicted as a stand-alone collection of elements in FIG. 9, a system of the invention may also be constructed from elements that are not physically connected, using, e.g., wireless communication. Additionally, various controllers may communicate with the catheter via a network, e.g., via the internet.

Methods of the invention, i.e., for removing thrombus from a vascular fistula are exemplified in FIGS. 10A-D. While FIGS. 10A-D depict clearing thrombus from an arteriovenous fistula, it is to be understood that the technique could be used to clear thrombus from other fistulas. The procedure begins with the placement of a guide wire 1005 through a venous entry 1010, e.g., via the antecubital veinas 1020, though the fistula 1030, and into the brachial artery 1040, as depicted in FIG. 10A. The placement of the guide wire 1005 is typically confirmed with a secondary imaging technique such as angiography (not shown). Once the guide wire 1005 is in place, a catheter 700 comprising an imaging element 310 and a disruption element 320 is directed along the guide wire 1005 to be delivered to the fistula 1030 needing treatment, as depicted in FIG. 10B. Once the catheter 700 has crossed the thrombus of the fistula 1030, the disruption element 320 is placed in position to disrupt the thrombus. The disruption element, shown in FIG. 10C as a balloon, is then actuated to create an actuated disruption element 325, shown in FIG. 10C as an expanded balloon, thereby disrupting the thrombus. After the thrombus has been disrupted, the disruption element is deactivated, and the treatment site is then assessed using imaging element 310, shown in FIG. 10D as an ultrasound imaging element. While FIGS. 10A-10D are used to depict disruption of thrombus prior to imaging, it is understood that the methods of the invention are not limited to a particular order, that is the fistula may be imaged prior to, or during disruption of the thrombus.

Furthermore, as discussed previously, the methods and systems of the invention need not be exclusively used for clearing thrombus from arteriovenous fistulas in hemodialysis patients. In instances where a patient does not have compromised renal function, it may be beneficial to additionally deliver thrombolytic agents to the patient before, after, or during the procedure. Thrombolytic agents are chemicals or compositions designed to erode, disrupt, or dissolve clotted blood, plaque, and/or fatty materials. Thrombolytic agents suitable for use with catheters of the invention include streptokinases, urokinases, and tissue plasminogen activators (TPAs) such as alterplase, reteplase, and teneteplase. The thrombolytic agents may be isolated from organisms where the agents naturally occur, such as Streptococcus, or they may be generated recombinantly and purified. In some embodiments, thrombolytic agents may be administered in conjunction with anticoagulants, such as heparin or Warfarin™ (Coumadin), or factor Xa inhibitors, such as rivaroxaban or apixaban.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. A system for increasing blood flow through a vascular fistula, comprising:
   a catheter comprising an imaging transducer and an expandable balloon, wherein the imaging transducer is disposed proximally of the expandable balloon;
   an imaging controller operatively coupled to the imaging transducer and configured to cause the imaging transducer to image the vascular fistula from inside the vascular fistula after disruption of a thrombus in the vascular fistula;
   a second controller operatively coupled to the expandable balloon and configured to actuate the expandable balloon thereby disrupting the thrombus in the vascular fistula, and increasing blood flow through the vascular fistula, wherein the second controller controls a pump delivering pressurized fluid to actuate the expandable balloon; and
   an image processing system operatively coupled to the imaging transducer and configured to (i) receive imaging data from inside the vascular fistula from the imaging transducer and output data corresponding to an image of a cross-section of the vascular fistula and (ii) determine changes in a boundary corresponding to an open cross-section of the fistula based upon the output data corresponding to the image; (iii) produce a boundary signal representative of an effectiveness of the disruption of the thrombus in the vascular fistula based upon the determined changes in the boundary; and (iv) direct the second controller to continue disrupting the thrombus if the boundary signal indicates that the thrombus remains in the vascular fistula.

2. The system of claim 1, further comprising a display configured to receive the data corresponding to the image of a cross-section of the vascular fistula and to display the image of a cross-section of the vascular fistula.

3. The system of claim 2, wherein the display is configured to display the boundary corresponding to the open cross-section of the fistula.

4. The system of claim 1, wherein the vascular fistula is an arteriovenous fistula.

5. The system of claim 1, wherein the imaging transducer is an ultrasound transducer.

6. The system of claim 5, wherein the imaging transducer is a phased array ultrasound transducer.

7. The system of claim 5, wherein the imaging transducer is coupled to a rotational pullback mechanism.

8. The system of claim 1, wherein the vascular fistula comprises a graft between a first and second blood vessel.

9. The system of claim 8, wherein the graft is an autologous graft.

10. A system for reducing a thrombus in a vascular fistula of a patient, the system comprising:
    a catheter comprising an imaging transducer and an expandable balloon, wherein the imaging transducer is disposed proximally of the expandable balloon;
    a balloon controller operatively coupled to the expandable balloon and configured to actuate the expandable balloon thereby disrupting the thrombus in the vascular fistula and increasing blood flow through the vascular fistula, wherein the balloon controller controls a pump delivering pressurized fluid to actuate the expandable balloon;
    an imaging controller operatively coupled to the imaging transducer and configured to cause the imaging transducer to produce first imaging data from inside the vascular fistula before actuation of the expandable balloon and second imaging data from inside the vascular fistula after actuation of the expandable balloon; and
    an image processing system operatively coupled to the imaging transducer and configured to (i) receive the first and second imaging data from the imaging transducer and produce output data corresponding to before and after images of a cross-section of the vascular fistula, respectively, that are each taken from inside the vascular fistula; (ii) determining changes in a boundary corresponding to an open cross-section of the fistula based upon the output data corresponding to the before and after images; (iii) produce a boundary signal representative of an effectiveness of the disruption of the thrombus in the vascular fistula based upon the determined changes in the boundary; and (iv) direct the balloon controller to continue disrupting the thrombus if the boundary signal indicates that the thrombus remains in the vascular fistula.

* * * * *